US011000265B1

(12) United States Patent
Ryu et al.

(10) Patent No.: US 11,000,265 B1
(45) Date of Patent: May 11, 2021

(54) STEERABLE BIOPSY NEEDLE WITH FIBER-ACTIVATED SHAPE MEMORY ALLOY

(71) Applicant: Intelligent Fiber Optic Systems, Inc., Santa Clara, CA (US)

(72) Inventors: Seok Chang Ryu, College Station, TX (US); Richard J. Black, Menlo Park, CA (US); Behzad Moslehi, Los Altos, CA (US)

(73) Assignee: Intelligent Fiber Optic Systems, Inc., San Jose, CA (US)

( * ) Notice: Subject to any disclaimer, the term of this patent is extended or adjusted under 35 U.S.C. 154(b) by 259 days.

(21) Appl. No.: 15/626,540

(22) Filed: Jun. 19, 2017

Related U.S. Application Data

(60) Provisional application No. 62/352,447, filed on Jun. 20, 2016.

(51) Int. Cl.
*A61B 10/02* (2006.01)
*A61B 34/20* (2016.01)

(52) U.S. Cl.
CPC .......... *A61B 10/0233* (2013.01); *A61B 34/20* (2016.02); *A61B 2034/2055* (2016.02); *A61B 2034/2061* (2016.02)

(58) Field of Classification Search
None
See application file for complete search history.

(56) References Cited

U.S. PATENT DOCUMENTS

| 5,321,257 | A * | 6/1994 | Danisch | G02B 6/02066 |
| | | | | 250/227.16 |
| 5,620,447 | A * | 4/1997 | Smith | A61B 17/32002 |
| | | | | 604/22 |
| 6,445,855 | B1 * | 9/2002 | Stowe | G02B 6/29334 |
| | | | | 385/126 |
| 6,872,433 | B2 * | 3/2005 | Seward | A61L 29/126 |
| | | | | 428/35.7 |
| 8,649,847 | B1 * | 2/2014 | Park | A61M 25/0158 |
| | | | | 600/433 |
| 2009/0099551 | A1 * | 4/2009 | Tung | A61B 5/103 |
| | | | | 604/530 |

(Continued)

*Primary Examiner* — Matthew Kremer
*Assistant Examiner* — Samuel C Kim
(74) *Attorney, Agent, or Firm* — File-EE-Patents.com; Jay A. Chesavage

(57) ABSTRACT

A biopsy needle has a cylindrical shell outer cannula and a stylet consisting of an inner stylet and outer stylet, both of which are inserted into the cylindrical cannula. The outer stylet has a series of strain relieved slits which provide bending over a deflection region in one direction, and the outer stylet is formed from a material such as a shape memory alloy (SMA) having a superelastic phase. The deflection is generated by an SMA wire spanning a deflection extent and attached to the outer stylet on either side of the deflection extent. The inner stylet, when positioned inside the outer stylet, has one or more actuation fibers which couple optical energy into the SMA wire or hollow SMA tube, causing a deflection of the outer stylet over the deflection extent, with the optical energy provided to the actuation fibers for control of the deflection. Additional fibers may be placed in the inner stylet to measure temperature and to measure deflection.

20 Claims, 4 Drawing Sheets

(56) References Cited

U.S. PATENT DOCUMENTS

| | | | |
|---|---|---|---|
| 2010/0069838 A1* | 3/2010 | Weber | A61M 31/002 |
| | | | 604/103.02 |
| 2011/0090486 A1* | 4/2011 | Udd | G01B 11/18 |
| | | | 356/73.1 |
| 2013/0084037 A1* | 4/2013 | Xia | B82Y 20/00 |
| | | | 385/12 |
| 2016/0270870 A1* | 9/2016 | Kowshik | A61B 34/71 |
| 2017/0281287 A1* | 10/2017 | Au | A61M 25/0113 |

* cited by examiner

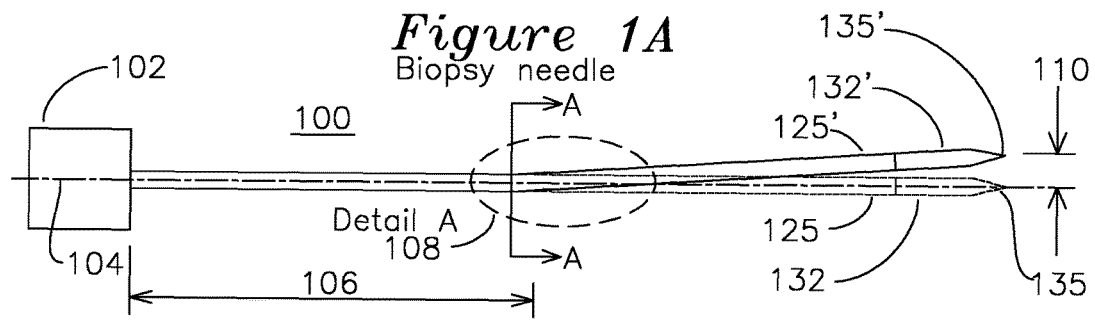
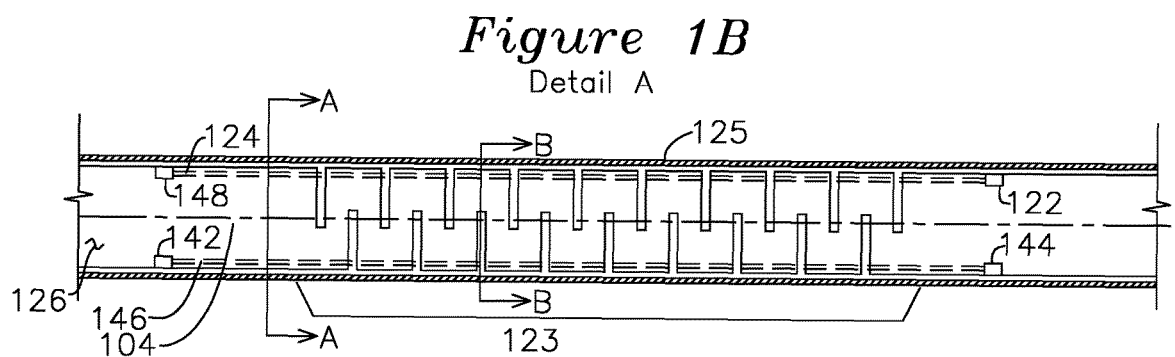
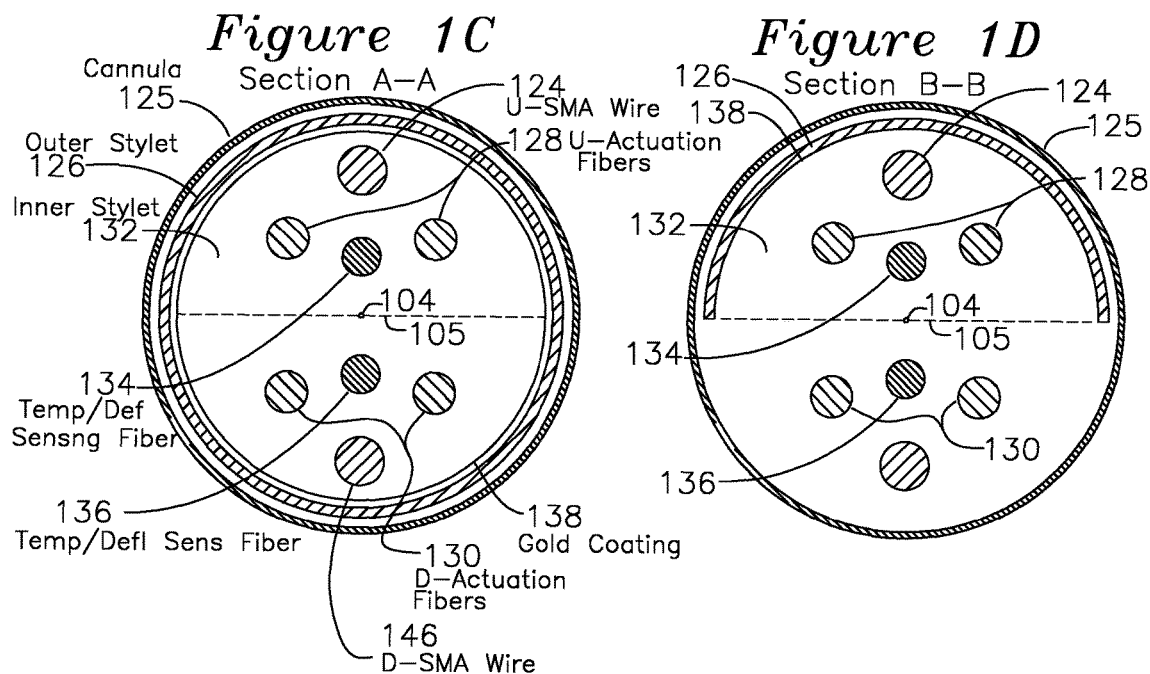

Side View — undeflected

Top View — undeflected

Side View — deflected

Section A-A

Section B-B

Steerable Biopsy Needle with Slitted Shape Sensing Fiber

STEERABLE BIOPSY NEEDLE WITH FIBER-ACTIVATED SHAPE MEMORY ALLOY

The present patent application claims priority to provisional application Ser. 62/352,447 filed Jun. 20, 2016.

FIELD OF THE INVENTION

The present invention relates to a biopsy needle. In particular, the invention relates to a biopsy needle which is steerable through symmetric deflection in a plane common to the central axis of the needle, and which provides for measurement of deflection angle using optical fiber sensing.

BACKGROUND OF THE INVENTION

In the field of interventional radiology, procedures such as biopsies or punctures are performed in combination with an imaging device which provides guidance during the biopsy procedure to a region of interest for the tissue sample. Magnetic Resonance (MR) scanners are useful imaging devices in this context: the radiologist and the patient are not exposed to any ionizing radiation, and the images provided by MR scanners provide a high level of contrast and sufficient resolution to identify small structures such as early stage tumors.

One of the factors limiting the accuracy of such guided biopsy techniques is needle deflection during the needle insertion. The control of the needle path, previously achieved with a rigid needle body assumption, thus evolved towards needle steering by including needle-tissue interaction models, to predict the behavior of the needle from its geometry and tissue modeling. In one prior art system, the needle is simply rotated by 180° when the estimated deflection reaches a given threshold. More complex control strategies have subsequently been developed to compensate for needle deflections and even to avoid anatomical obstacles. In another prior art system, the needle is manipulated from its base, outside the patient body, using a robotic system to create forces and moments on the needle in a similar way to the approach used by clinicians. The stiffness of the tissues at the entry point may limit such a steering strategy, and a robotic system relying on this technique would require mobility in addition to those required for needle insertion and rotation about the needle central axis.

In another prior art device, relative displacements between concentric needles, or a pre-bent needle integrated into a straight cannula, are used to generate a needle trajectory.

The design of an active needle has long been considered of interest, but a primary difficulty for guided use is MR compatibility, due to the interaction between the needle and the magnetic field and RF fields generated by the MR scanner. For example, one prior art system uses a needle with a magnetized compliant section near the tip that is controlled by an external magnetic force, which is not MR-compatible. The thin tip also makes the needle susceptible to buckling. Another prior system utilizes a piezoelectric material deposited on the needle to create a continuous bending effect along the needle. However, this design is not optimized for steering the needle tip during insertion. Another prior art system uses a tendon-driven steerable needle, and has been used for lung biopsy procedures, where tissues are much less dense than in the prostate.

The principle of an active needle can also be related to active catheters for navigation in blood vessels, however this type of design cannot be directly exploited for an active needle because of the very different mechanical interactions that exist between a needle and tissues, as compared to the controlled movement of a catheter which is guided by vessel walls.

MR-compatible actuation technologies have also been developed for robotic devices. Pneumatic or hydraulic actuation systems are of interest, the latter presenting an impressive power/volume ratio. However, integrating such technologies in a 1-2 mm diameter needle has not been possible and specific new risks to the patient are presented by the introduction of these methods in a needle biopsy requiring a higher level of active guidance and steering.

It is desired to provide an MR compatible needle which is steerable through a combination of bi-directional needle deflection and rotation about the needle central axis during and throughout the needle insertion process and provide guidance to a biopsy site.

OBJECTS OF THE INVENTION

A first object of the invention is a guided biopsy needle having an outer sleeve cannula surrounding a removable steerable stylet comprising an outer stylet part and an inner stylet part, the outer stylet part having a central axis and a medial plane which lies on the central axis, the outer stylet part also having a plurality of slots which are perpendicular to the central axis, the slots having an extent which passes through the medial plane, the slots optionally formed on either side of the medial plane to provide elastic bi-directional bending of the outer stylet in a plane perpendicular to the medial plane, the slots being placed over an axial extent, the outer stylet part further having a shape memory alloy (SMA) which is anchored on opposite ends of the axial extent of slots such that when the SMA is thermally activated, the needle deflects in a direction which reduces the gaps of the slots on one side of the medial plane or on the opposite side of the medial plane, the inner stylet having longitudinal actuation fibers for coupling photonic energy to the SMA, the inner stylet also having a temperature sensor and a deflection sensor, the actuation optical fiber being either located inside a cylindrical SMA which surrounds the optical fiber, or the actuation optical fiber being located adjacent to the SMA, the actuation optical fiber coupling optical energy to the SMA.

A second object of the invention is a guided biopsy needle having an outer stylet and an inner stylet, the outer stylet having:
a base portion attached to the outer stylet and having a cylindrical hollow extent, a first SMA anchor extent, a deflection extent, a second SMA anchor extent, an SMA material attached in the first SMA anchor extent and also the second SMA anchor extent, the SMA material thereby spanning the deflection extent;
the inner stylet having:
a cylindrical SMA tube placed on at least one side of a medial plane;
at least one actuation optical fiber coupling optical energy to the SMA placed inside and coaxial to the cylindrical SMA tube;
at least one optical fiber for measuring a temperature; and at least one optical fiber for measuring a deflection.

SUMMARY OF THE INVENTION

A biopsy needle has an outer cannula and a removable stylet, the stylet comprising an inner stylet part and an outer stylet part, both of which are inserted into the cannula for steering and shape sensing, such as during a biopsy procedure. After steering the needle to the desired location, the stylet assembly is removed and a biopsy needle is inserted into the cannula for tissue sampling. The outer stylet is formed from a cylindrical shell or tube and has, in sequence, a base attachment extent, a first extent, a first SMA attachment extent, a deflection extent, a second SMA attachment extent, a second needle extent, and optionally, a tip, all of which are formed about a central axis of the biopsy needle. On at least one side of a medial plane, and optionally on both sides of a medial plane which includes the central axis, SMA material is secured to the first SMA attachment extent and second SMA attachment extent, thereby spanning the deflection extent.

Typical SMA materials include the alloy Nickel Titanium (NiTi) also known as Nitenol where Nickel and Titanium are present in approximately equal atomic percentages. NiTi is a preferred for biomedical applications because of its biocompatibility with human tissue, absence of ferromagnetic response providing MR compatibility, and high force per unit area functional performance. An alternate SMA is an alloy of copper-aluminum-nickel.

The inner stylet fits inside the outer stylet and the inner stylet also accommodates the SMA material, the inner stylet also having adjacent actuation optical fibers with a cladding and/or core modified to couple photonic energy into the SMA, causing a rise in temperature in the SMA, and for the SMA to contract, thereby deflecting the needle. In one example of the invention, the SMA material is formed into a cylinder, with an actuation optical fiber positioned inside the cylinder. The distal end of the inner stylet may terminate in a needle tip, such that the needle tip may be formed from the outer stylet with the inner stylet placed inside the outer stylet, or the needle tip may be formed from the inner stylet, and thereafter placed into the outer stylet to form the removable stylet assembly. The cladding and/or core modification of the actuation optical fibers may include etching or side polishing of the cladding of multi-mode fibers to allow regions of optical emission coupling to the SMA, or tilted fiber gratings written into single mode fibers which couple optical energy to the SMA, or a combination of the above. The outer stylet may also be formed from an SMA with a superelastic mode to increase deflection during the photonic actuation state, or the outer stylet may have a series of grooves on one, or both sides, of the medial plane. The inner stylet additionally provides structures for preferential coupling of actuation optical energy into the SMA material, and in one embodiment, includes a reflective coating on the outer cylindrical surfaces of the stylet which increase the coupling of actuation energy from the actuation optical fiber to the SMA material. The inner stylet also provides for a temperature measurement sensor and a deflection sensing fiber.

In one embodiment of the invention, the actuation fiber is a multi-mode optical fiber with internal angled gratings formed in the core of the fiber which couple optical energy out of the fiber and to the adjacent SMA, or the SMA which surrounds the optical fiber, and the temperature sensing fiber may comprise a fiber Bragg grating (FBG) which is coupled to a single port wavelength interrogator for measurement of the deflection, with the temperature measurement used to limit the actuation energy level and also compensate for measurements made with the deflection sensing fiber.

The multiplexed fiber optic sensors of the present invention allow distributed, multifunctional sensing and actuation in a small volume, allowing for application in 20 gage needles. The use of guided wave optics in a flexible fiber optic format allow for non-line-of-sight application (any procedure requiring needle bending), greatly expanding the list of possible in vivo uses. The steering and sensing of the present invention significantly enhances needles already in widespread use, occupying a small volume within the needle, allowing for rapid familiarization by surgeons.

BRIEF DESCRIPTION OF THE DRAWINGS

FIG. 1A is a side view of a biopsy needle.
FIG. 1B is a detail side view of a steering region of the needle.
FIG. 1C is a section view of FIG. 1B through A-A.
FIG. 1D is a section view of FIG. 1B through B-B.

DETAILED DESCRIPTION OF THE INVENTION

Figure 1E:
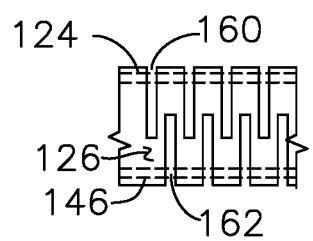
FIG. 1E is a side view of an undeflected biopsy needle.

FIG. 1A shows the active elements of a steerable biopsy needle 100, including a cannula 125 which is optionally covered with a Teflon sheath or tube (not shown) to provide thermal isolation between the surrounding tissues and the thermally activated elements of the needle. FIG. 1A is best understood in combination with detail A FIG. 1B, and section views 1C and 1D. According to a general object of the invention, the needle is steered using an axial asymmetry of internal force which is coupled to the outer stylet 126 of the needle to create forces on the needle during its insertion. In this embodiment, the primary degrees of freedom to control needle direction are the insertion geometry and the axial rotation of the needle. Needles with asymmetric bevels at the tip are submitted to an unbalanced field of forces during the insertion. This phenomenon can be used to steer thin needles. Various complex insertion trajectory curves may be obtained by combining the needle insertion and self-rotation movements about the central axis 104 of the needle in combination with a needle tip deflection 110. The region of deflection 108 of detail A may be placed a distance 106 from the needle base 102, which is rotated during placement and deflection to guide the biopsy needle to the desired location.

The biopsy needle of FIG. 1A is capable of active bending that, in combination with the normal insertion forces and the ability to rotate the needle about its central axis 104, allows it to be steered to reach small tumors or other sites. The actuation system which will be described is entirely compatible with MR imaging and the overall needle diameter in one embodiment is 1.65 mm, which is compatible with standard prostate biopsy needles.

Among the actuation technologies that present a high power/volume ratio and MR-compatibility, Shape Memory Alloys (SMA) are of particular interest, and when formed as a wire, or as a cylindrical shell, provide a high specific force combining a large mechanical strain with a large force to volume ratio. By activating thermally a phase transition in the SMA microstructure, this material can be used as an actuator, and in one embodiment, the thermal actuation is accomplished using optical energy.

Joule heating with an electric current is one method of actuation to obtain SMA contraction. An MR-compatible device can be designed using such an approach. However, imaging artifacts will be created from the co-generated SMA current magnetic fields if actuation and MR imaging are performed concurrently.

The present biopsy needle of the present invention provides an outer cannula 125, into which is inserted a stylet composed of two main parts as shown in the views of FIGS. 1A, 1B, 1C, and 1D: an inner stylet 132 and an outer stylet 126. During a biopsy, the two stylet elements 132 and 126 are inserted together into the cannula 125 to form the biopsy needle, and the stylet is activated to steer and sense the shape of the needle as the needle assembly is guided to reach the biopsy site. Then, the stylet comprising the outer stylet 126 and inner stylet 132 are removed together, and a biopsy probe is inserted through the cannula 125 to perform the biopsy. In one embodiment of the invention shown in FIGS. 1A, 1B, 1C, and 1D, the active elements include upper SMA wire 124 attached to the outer stylet 126 on opposite sides of a deflection extent 123 and anchored outside the deflection extent at regions 148 and 122, the upper SMA wire 124 which is activated by optical energy conveyed by adjacent fibers in the inner stylet 132 which couple to the outer stylet 126 and steer the cannula 125. A lower SMA wire 146 is anchored at ends 142 and 144 beyond the deflection extent, and the lower SMA wire 146 is similarly (and typically exclusively) activated by optical fibers conveyed by adjacent fibers in the inner stylet which coupled to the outer stylet 126 and steer the cannula 125 in the opposite direction from the upper SMA wire 124, bending the needle below the medial plane 105. The inner stylet 132 and outer stylet 126 are separate coaxial structures such that the outer stylet 126 deflection is not impeded by the inner stylet 132 during deflection, and it is preferable for friction between the outer surface of the inner stylet and the inner surface of the outer stylet be minimized, and the photonic coupling from actuation fibers 128 and 130 to the SMA wire 124 to be maximized. In a preferred embodiment, the tip extent of the needle includes tip 135 which is formed from a metal such as stainless steel or any biocompatible material and fastened to a distal end of the multi-lumen inner stylet 132, and the needle tip 135 tapers to a point on the main axis 104, although it is possible for the tip 135 to form a point adjacent to the outer radius of the stylet, such as a prior art planar beveled cut at the needle tip.

The active element SMA wires 124 and 146 introduce one degree of bidirectional freedom in the needle body. Combining active bending with needle insertion and axial 104 rotation movements, it becomes possible to control the needle trajectory, following a similar approach as used previously for needle steering with beveled tip needles. Upper SMA wire 124 which is activated by upper actuation fibers 128 allows steering to regions above medial plane 105, and lower SMA wire 146 which is activated by lower actuation fibers 130 allows steering to regions below medial plane 105.

In a preferred embodiment, the inner stylet 132 has a maximum diameter of substantially 1.35 mm, corresponding to an 18G biopsy needle. With the outer stylet 126 and external cannula 125, the overall diameter is equal to 1.65 mm, which is equivalent to 16G devices used for prostate biopsies.

FIG. 1C shows a cross section view A-A of FIG. 1B, and FIG. 1D shows a cross section view B-B through one of the slotted strain relieved cuts in the deflection extent 123. The upper actuation SMA 124 is formed as a wire with attachment points outside of the deflection extent 123, such as at upper SMA attachments 124 and 122, formed onto the inner or outer stylet. The lower actuation SMA 125 is also formed as a wire on the opposite side of medial plane 105 with lower attachment points 142 and 144 on the inner or outer stylet, which may be in the same axial extent and opposite the attachment points 124 and 122. The upper SMA wire 124 is activated with side optical heating through photonic energy coupled into adjacent actuation fibers 128 and 130. To promote compactness and effective heat transfer, the actuation optical fibers 128 and 130 run parallel to the needle axis 104 and transmit heat over a finite length of the SMA wire 124 such as the deflection extent 123 and oriented in the central axial 104 direction to get a sufficient needle displacement (shown as FIG. 1A deflected components 132' and 125' compared with undeflected components 132 and 125). Additionally, to improve photonic coupling from the actuation fibers 128, 130 to the SMA 124, the outer surface of the inner stylet 132 (or inner surface of the outer stylet 126) may be coated with a reflective material 138 such as gold which reflects infrared (IR) optical energy, the coating excluding the slot in the stylet supporting the SMA wire 124, to ensure that optical energy from the actuation fibers 128 and 130 is optimally coupled into the SMA wire 124 and is not lost to leakage outside the stylet 132. It may also be desirable to provide a reflective interface at the medial plane 105 such that optical energy from the upper actuation fibers 128 do not couple to the lower SMA 146, and that optical energy from the lower actuation fibers 130 does not couple to the upper SMA wire 124, as well as the addition of thermal isolation to prevent cross coupling of thermal energy from one half to the other. Several different forms of actuation fibers 128 and 130 are possible for coupling optical energy from the actuation fibers 128 or 130 to the upper SMA 124 and lower SMA 146, respectively.

In one embodiment of the invention, the actuation fibers 128 and 130 are multi-mode fibers and have a cladding which is reduced in thickness on one or more regions along the axis with the regions oriented towards the SMA wire 124 to allow optical energy guided in the core to couple into the SMA wires 124 and 146. In an example embodiment, the optical fiber cladding has a diameter of 125 µm, which is removed in specific regions of the fiber using a glass etching cream such as Armour Etch of Armour Products. In another example, the etching of a particular region is performed in successive etching and rinsing events, with each successive session removing substantially 6 µm of cladding. In another example, the etch process produces a region extent greater than 2 mm for coupling optical energy out of the core of the actuation fiber. In another example of the invention, the cladding is removed and a plurality of discrete regions of the actuation fiber 124 are etched, such as in etching time intervals of substantially 30 minutes, each interval removing substantially 6 µm of cladding from a fiber having a cladding diameter of approximately 125 µm and a fiber core diameter of approximately 105 µm. In a preferred embodiment of the invention, each etching region has a depth of etching which provides levels of optical energy to exist at each region, thereby providing a substantially uniform optical excitation over the extent of the SMA wire 124. In another embodiment of the invention, each successive etched region has a different etch extent, such that each successive etch region is greater than a previous region, thereby providing a uniform level of optical energy by compensating for the reduced optical energy which leaves each etch region to the subsequent etch region. Although the dimensions given correspond to those of a multi-mode fiber, it is possible to consider a single mode fiber for actuation using reduced thickness cladding as described.

In another example of the invention, the actuation fibers are multi-mode fibers which are side polished to increase the optical coupling from the core to the actuation wire 124, with the same objectives of uniform levels of power being applied to the SMA wires 124 and 146 along the active extent 124 of the SMA wire 124 and 146, or any preferable extent of the SMA wire which provides the required contraction in the SMA wire 124 and 146. It is understood that activation of SMA wires 124 or 146 is typically performed exclusively to achieve an upward or downward deflection.

In another example of the invention, the optical energy is coupled out of the actuation fibers 128 and 130 and into the SMA wire 124 through the use of tilted fiber Bragg gratings (TFBG) written into single mode fiber (SMF). For TFBGs, by removing the fiber cladding and writing an angled grating into the core of the fiber, the power emission of optical energy entering the SMA wire 124 from the actuation fiber 128 or 130 is maximized, and can reach 55% of the laser power emitted through the fiber. In this manner, homogeneous photonic emissions leading to SMA heating can be obtained over lengths up to 50 mm of fiber. Whether side polishing or TFBGs are used, the addition of thermal cement can enhance the uniformity of thermal transfer along the SMA wire. It is also desirable to ensure that maximum coupling of optical energy out of the actuation fiber and to the SMA wire 124 is achieved, and that a minimum of input optical energy is coupled back to the source, as the optical source is typically a laser with an isolation requirement providing a minimum of reflected optical energy enter the laser output port, which tends to cause modal changes and other irregularities in temporal uniformity. A linearly polarized laser optical source may reduce this isolation requirement.

To enhance uniform thermal coupling of optical energy to the SMA fiber 124 where specific regions of emission are used, the specific regions of optical side emission along the axis of the actuation fibers may be staggered. For example, if each actuation fiber has four discrete regions of optical emission, and the four regions are directed in the same azimuthal angle of the fiber axis, and the axial separation is D between emitting regions, the two fibers may be axially offset from each other by a distance of D/2, thereby providing optical energy every D/2 axial distance over the actuation extent of the SMA wire 124.

In one embodiment of the invention, the use of SMA materials for MR compatible guidance is also used to provide superelastic structures in outer stylet 126. The phase transition of SMA 124/146 may be used for actuation, but also in the outer stylet 126 to provide the flexibility needed to deflect the needle. SMA exhibits a so-called superelastic domain known as the austenite phase when the SMA temperature is sufficiently high. A stress increase can then induce a phase transition towards the martensite phase. This stress-induced phase transition is characterized by a large plateau in the stress-strain domain, providing increased deflection for a given applied force. In one embodiment of the present invention, this large elasticity domain is optionally used for the outer stylet 126 or inner stylet 132 of the active device. This approach allows the needle to achieve high deflections, due to device actuation or to interaction with tissues, and without plastic deformation.

Figure 1F:
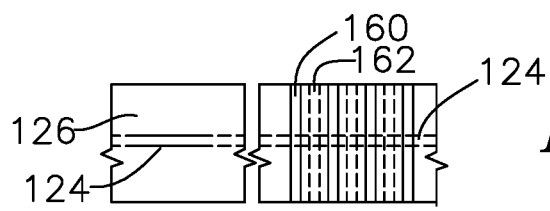
FIG. 1F is a top view of an undeflected biopsy needle.
Figure 1G:
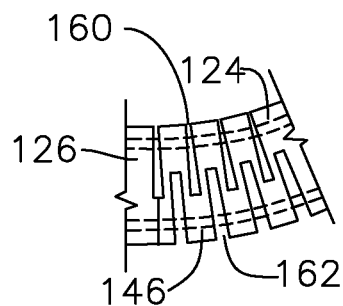
FIG. 1G is a side view of a deflected biopsy needle.

In one embodiment of the invention as shown in FIGS. 1B, 1C, 1D, 1E, 1F, and 1G, the actuation mechanism is based on a laser machined SMA tube which forms the outer stylet 126 and SMA wires 124/146 which forms the active element attached to the outer stylet in first attachment extent 148 and second attachment extent 122. The flexible axial deflection extent 123 of the outer stylet 126 is formed from tube stock SMA tube is 25 mm long, with a series of slits 160 formed primarily on an upper half of the medial plane 105 and a series of opposite slits 162 formed primarily on a lower half of the medial plane 105, as shown in FIGS. 1E and 1F. The slits may terminate in rounded or other non-angular cuts to minimize stress concentration in the outer stylet 126 material at bending points. The number of slits 160/162 and the slit gap of 30 µm between two consecutive slits are chosen so that the nominal 30 µm gap of each slit closes fully under maximum actuation. In this way, the device is always in a configuration for which the wire can generate a tension during its contraction, independent of the external interaction forces. Once the slits have closed (in the fully deflected position), the needle assembly becomes considerably stiffer with respect to additional bending loads. FIG. 1F shows exemplar anchor extents 148, 122, 142, or 144 at an end of the outer stylet 126 which is created in one example shown by two holes 150 with the upper or lower SMA wires 124 or 146 secured by threading the SMA wires 124/146 through each hole 150. In an alternate embodiment, the SMA wire 124/146 anchoring is accomplished using a weld or other bond which minimizes stress concentrations at the anchor points of SMA wire 124/146 which could reduce the SMA wire life.

In addition to the SMA wires 124/146, which in a preferred embodiment are substantially 0.254 mm, the outer stylet 126 is formed from an SMA tube which is in close proximity to (as in FIG. 1C), or encloses (as in FIG. 2A/B), the various optical fibers for SMA actuation through heating and sensing through stress induced in the SMA wire 124/146 from the actuation fibers 128, 130. These elements, presented in the following section, are inserted in a flexible multi-lumen polytetrafluoroethylene (PTFE) tube which forms the body of stylet 132 to obtain and maintain their alignments. High density PTFE material is relatively transparent to infrared (IR) light, which in the present patent is understood to be in the range from 800 nm to 2500 nm wavelength, although actuation optical fiber operates at preferably lowest attenuation in approximate wavelength ranges of 1550 nm±50 nm. Typical single mode optical fiber has greater attenuation at shorter wavelengths, however economical optical sources operate in the 850 nm and 1300 nm wavelength ranges compared to 1550 nm sources. This IR transparency allows most of the emitted power from the actuation fibers 128 and 130 to reach the SMA wires 124/146. A sputtered 500 nm gold coating 138 on the outer surfaces of the stylet 132, excluding the slot which supports SMA wire 124, enhances coupling of IR which is internally reflected in the stylet 132 to the SMA wire 124. In one embodiment of the invention, the stylet 132 is extruded high density PTFE resin with the extrusion die forming the slot for SMA wire 124/146, and channels for actuation fibers 128 and 130, temperature sensing fiber 134, and deflection sensing fiber 136. In another embodiment of the invention, the stylet is fabricated from surgical grade silicon. The tip 132 is typically fabricated from a metal such as stainless steel and bonded to the distal end of the stylet.

In one embodiment of the invention, the SMA wire has a diameter of substantially 0.25 mm. In a preferred embodiment, Flexinol® wire manufactured by Dynalloy of Irvine, Calif., US is used, which can generate, according to the manufacturer's specifications, up to 4% of strain when heated to 90° C., and the optical energy delivered to the actuation fibers 128, 132 is provided by in infrared source such as a 976 nm laser providing greater than 0.5 W of power to each actuation optical fiber for distributed delivery to the SMA wire 124. The 90° C. temperature is high compared to safe temperatures for human tissues, which are on the order of 45° C. However, in a preferred embodiment, at least one of the active element SMA wire 124/146 or superelastic deformation region 124 of the outer stylet 126 formed from SMA is heat treated to lower the phase transition temperature to 55° C. In a preferred embodiment of the invention, the outer stylet 126 is coated or placed inside a tube formed from PTFE, which introduces an additional thermal insulation with respect to tissue. Moreover, the bending actuation will be applied only for short periods of time, to alter the path taken by the needle as it is inserted. Under these conditions, surrounding tissues would be able to sustain the resulting temperature increases. Two actuation fibers, 128 and 130, are embedded in the device to heat the SMA wire 124, or alternatively, are placed inside SMA cylinders. Each actuation fiber integrates a side heating element so that four heating areas, including the actuation optical fiber tips, are positioned along the 18 mm extent 123 of SMA wire.

Figure 2A:
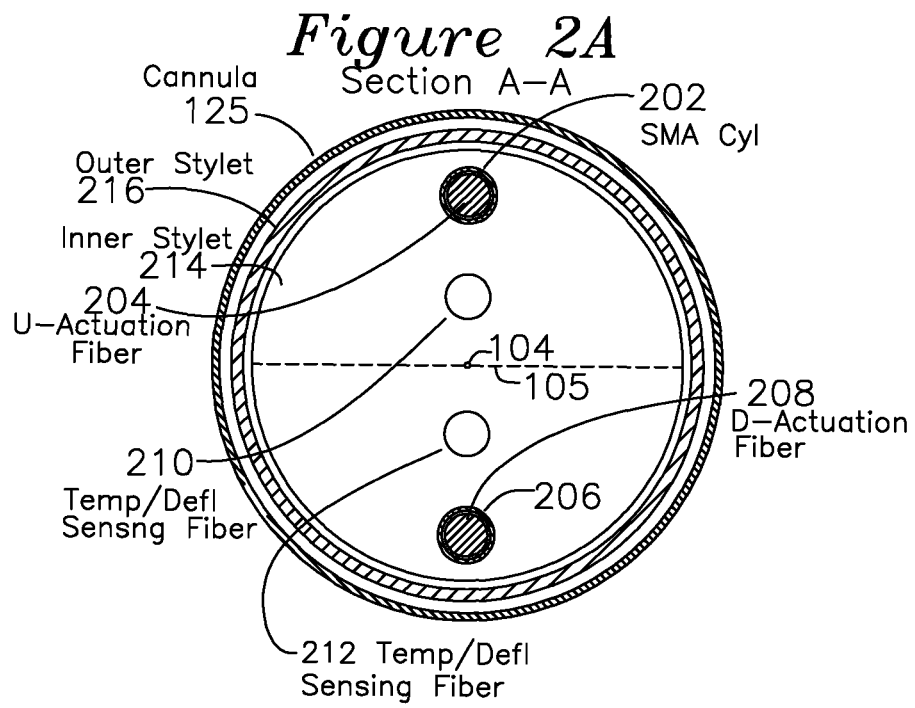
FIG. 2A is an alternative embodiment of the invention through section A-A of FIG. 1B.
Figure 2B:
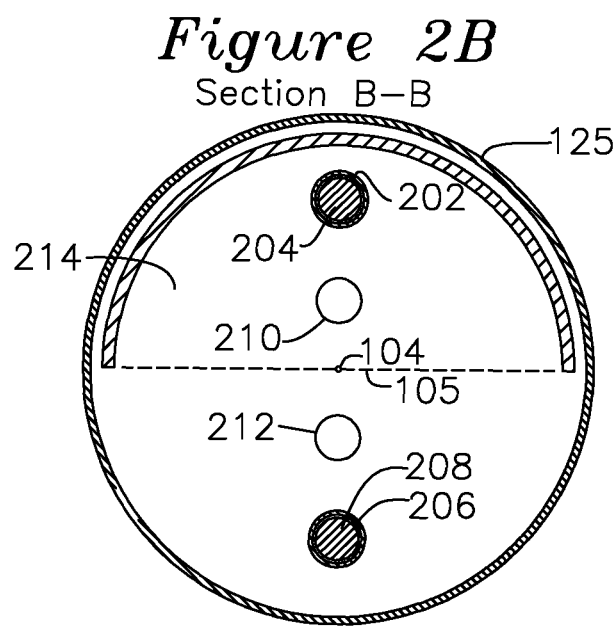
FIG. 2B is an alternative embodiment of the invention through section B-B of FIG. 1B.

FIGS. 2A and 2B show an alternative embodiment of the invention of FIGS. 1A and 1B, where the actuation is performed by upper hollow SMA cylinder 292 and lower hollow SMA cylinder 206, each of which carry respective actuation optical fibers 204 and 208, respectively. FIG. 2A shows a section view A-A of FIG. 1B and FIG. 2B shows a section view B-B of FIG. 1B, with the hollow SMA cylinder being actuated by the respective enclosed actuation optical fiber. This actuation system has greatly improved coupling efficiency of optical energy from the fiber to the SMA cylinder for improved actuation efficiency. Attachments of the ends of the SMA cylinders to the outer stylet 216 (equivalent to outer stylet 126 of FIG. 1C) at attachments 148, 122, 142, and 144 may be similarly made, with provision for the actuation optical fiber to pass through the attachment point and to an external optical source. As before, temperature or sensing fiber gratings 210 and 212 may be placed in the inner stylet 214 (functionally equivalent to inner stylet 132 of FIG. 1C). As the actuating optical energy from actuation optical fibers 204 and 208 radiating inside the SMA actuator cylinders 202 and 206 is concentrated within those SMA actuator cylinders, the inner stylet material optical properties are not important, and there is no need for a reflective gold layer as in FIGS. 1C and 1D. Actuation optical fibers 204 and 208 may have a cladding diameter in the range of 80-125 μm containing an angled (tilted) FBG (where the tilt angle can vary between 6 to 45°), where the fiber with angled grating is inserted in the hollow core of the Ni—Ti actuators 202 and 206. The angled gratings may be formed by writing the gratings through the jacket using an 800 nm femtosecond pulse to create the angled FBGs. This write-through-jacket method leaves the optical fiber jacket completely intact, thereby eliminating the risk of fiber failure due to damage that can occur when the jacket is temporarily removed for the writing of gratings. The total axial extent of optical fiber is covered by tilted FBGs which produces a uniform temperature profile.

In another example of the invention of FIGS. 2A and 2B, the tilted FBGs may not only produce heat and radiate it to the surrounding SMA actuator tubes 202 and 206, but also measure the temperature inside the Ni—Ti tube by using the same or other regions of the grating, optionally formed as gratings operative in other wavelengths, to measure strain, temperature, or deflection. This sensor would replace grating sensors of fibers 212 and 212. As a result of the design of FIGS. 2A and 2B, 80% of the light is absorbed in the first pass and the remaining 16% is absorbed in the return trip. In this manner, the Bragg mode effect can be used as a heating sensor and in situ thermometer simultaneously.

In an example preferred example of the invention, the SMA actuators are used in a tension mode, whereby thermal activation can be channeled efficiently into axial contraction forces positioned adjacent to a deflection surface of the outer stylet, preferably adjacent to an inner surface of the outer stylet. This results in simpler and more controllable activation dynamics compared to prior art approaches that use pre-curved SMAs to activate a steerable needle.

Accordingly, MR-compatible optical sensing of position is provided. In addition to the actuation fibers 128 and 130, a temperature sensing optical fiber 134/136 of FIGS. 1C and 1D, or 210/212 of FIGS. 2A and 2B, with standard FBGs provides temperature sensing. In one embodiment of the invention, at least one sensor 134/136 or 210/212 is a deflection strain sensing fiber 136 has a treated section which increases light loss as a function of curvature. Such a shape sensing fiber can be constructed by coating the distal tip (closest to the needle tip 135) of the fiber with sputtered gold, machining a series of slits into the cladding and which are perpendicular to the axis of the fiber, such that bending the fiber reduces or increases the optical loss for reflected optical energy, illuminating the opposite end of the fiber through a coupler or circulator, and measuring the reflected optical energy to the other port of the circulator. In one example embodiment of the invention, the shape sensing fiber is unjacketed plastic fiber with 250 μm cladding diameter, and 240 μm core diameter, with eight slits having a spacing of 300 μm, starting 10 mm from the needle tip, centered on the active element SMA wire 124, with the tip polished with 1 μm abrasive and sputter coated with a 500 μm deposition layer of gold. On advantage of the shape sensing fiber fabricated in this manner is that it may be placed into the lumen of the stylus freely, as it does not need to be anchored in the lumen as is the case with FBG gratings measuring strain, with the fiber bonded to the lumen at one end to prevent rotation of the bending sensor in the lumen.

In one example of the invention, the temperature/deflection sensing optical fibers 134 and 136 are bonded to the inner stylet 132 and have FBGs formed therein, thereby providing a differential strain measurement (one FBG shifting up in wavelength, one FBG shifting down in wavelength), thereby indicating needle deflection. In another example of the invention, the optical fibers 134 and 136 include an unbonded region which contains a temperature measurement grating which is used to compensate the associated strain measurement made in the bonded region of the FBG. Position sensing of the deflected needle may additionally be performed by placing a multi-core optical fiber in the medial plane 105 of the central axis 104, each of the multi-core optical fibers having an FBG which is bonded to, and positioned on, a respective side of the medial plane 105 of the inner stylet 132, such that the wavelength shift of each FBG is measured to determine a needle bend or deflection. Temperature measurement to compensate the strain measurement may be performed using an unbonded region of the fiber which contains a temperature measurement FBG.

In another embodiment of the invention, at least one of the sensing fibers 136 or 136 of FIGS. 1C and 1D or 210 or 212 of FIGS. 2A and 2B senses stain and has an FBG embedded in a location which senses strain during elongation, thereby providing a reflected wavelength shift which can be used, in combination with a temperature measurement such as from fiber 134, to determine a deflection. The estimated curvature information can be converted into mechanical strain along the temperature sensing fiber 134 and the SMA wire 124. The strain-compensated temperature and the strain on the SMA wire 124 enable closed loop control of bending angle. This bending angle can also be used to estimate the needle shape, for instance to track the needle tip in the image plane.

One embodiment of the invention provides for dual-mode gratings, which may be formed in several different ways, as will be described. It is known that estimating strain in an FBG from the shift in reflected FBG wavelength requires an accurate temperature measurement to compensate for wavelength shift associated with temperature gradients and drifts. For the configuration of FIGS. 1C and 1D (or FIGS. 2A and 2B), such as where sensor 134 (or 210) is a temperature sensor and sensor 136 (or 212) is a strain sensor, both formed as FBGs, it may occur that a temperature gradient exists from actuating fibers 130 and 128 (or 204 and 208) to strain sensing FBG 136/212, such that temperature sensing FBG 134/210 is not able to accurately sense the temperature of strain sensor 136/212 to provide temperature compensation information. To solve this problem, in one embodiment of the invention, "dual mode gratings", or dual mode FBGs with different wavelength responses may be written in the same sensing region of optical fiber 136, such that reflection of two different wavelengths occurs. In this mode of operation, each dual mode FBG reflects wavelengths according to the differential relationship:

$$\Delta\lambda 1 = \alpha 1 * \Delta T + \beta 1 * \Delta S$$

$$\Delta\lambda 2 = \alpha 2 * \Delta T + \beta 2 * \Delta S$$

where:

$\alpha 1$ and $\alpha 2$ are temperature coefficients for wavelengths $\lambda 1$ and $\lambda 2$, respectively, which are typically known a priori or are characterized;

$\beta 1$ and $\beta 2$ are strain coefficients for wavelengths $\lambda 1$ and $\lambda 2$, respectively, which are typically known a priori or are characterized;

$\Delta T$ is the temperature change for the dual mode grating; and $\Delta S$ is the change in strain for the dual mode grating.

Using the above linear relationships, it is therefore possible to make a single measurement of the two reflected optical wavelengths $\Delta\lambda 1$ and $\Delta\lambda 2$, and solve for $\Delta T$ and $\Delta S$ from prior knowledge of $\alpha 1$, $\alpha 2$, $\beta 1$, and $\beta 2$. As is known in the art of solving linear equations, the resolution of wavelength or temperature is improved when the ratio of $\alpha 1/\alpha 2$ and $\beta 1/\beta 2$ is maximized or minimized. In this manner, a single dual mode FBG may be used for fiber 136/212, which removes the need for temperature measurement fiber 134/210. In another embodiment of the invention, dual mode gratings can be formed from a single FBG having one reflection response at $\lambda 1$, and using the second natural response at the half wavelength response $\lambda 2 = \lambda \frac{1}{2}$, and relying on the different $\alpha$ and $\beta$ coefficients at these two separated wavelengths. In another dual mode grating embodiment of the invention, two separate optical fibers with maximized or minimized $\alpha 1/\alpha 2$ and $\beta 1/\beta 2$ coefficient ratios are spliced together and have FBGs written on them such that the two separate gratings span the same sensing region, thereby providing that the two reflected wavelengths $\lambda 1$ and $\lambda 2$ can be in the same wavelength region, and relying on the coefficient ratios between the two types of fibers for improved resolution.

Steering performance is intrinsically linked to the steering control strategy and the mechanical properties of the tissues in interaction with the needle 100. A first mechanical property is the maximum deflection of the needle when no force is applied on the needle tip. This deflection describes the achievable trajectory correction when using a simple retract-reinsert strategy, where the needle is almost completely retracted, deflected, and inserted again. The second mechanical property is the needle stiffness, which is estimated using a very simple interaction model based on the potential behavior of the device in tissue.

Figure 3:
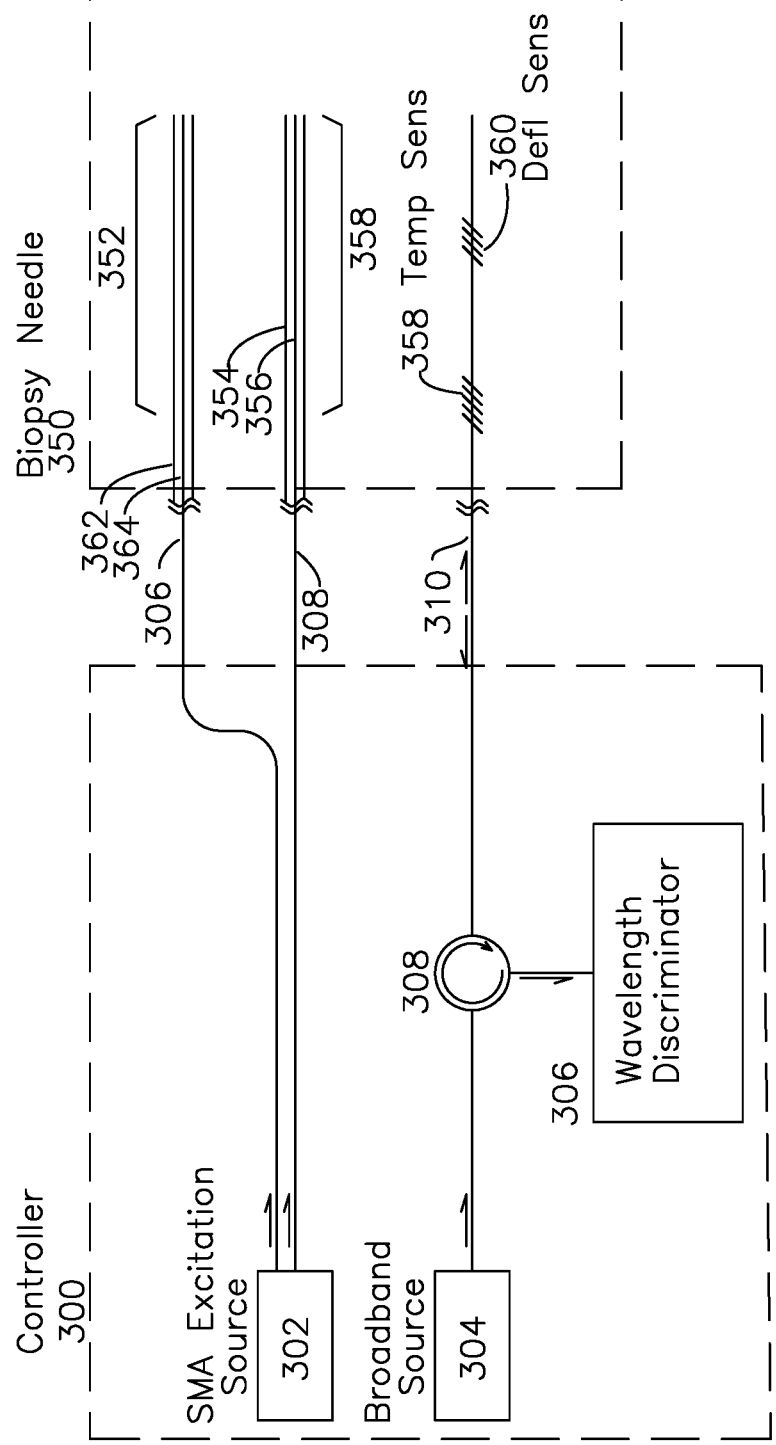
FIG. 3 is a block diagram of a controller coupled to a steerable biopsy needle.

FIG. 3 shows an example all-optical needle deflection and shape sensing controller 300 coupled to a biopsy needle 350 such as was previously described in preceding FIGS. 1A 1B, 1C, 1D, and 1E, or FIGS. 2A and 2B. Actuation fibers 306 and 308 are exclusively actuated, with upper actuation fiber 306 coupled to actuation fibers 128 of FIG. 1C or 1D, or to 204 of FIGS. 2A and 2B, and lower actuation fiber 308 coupled to lower actuation fibers 130 of FIGS. 1C and 1D, or to 208 of FIGS. 2A and 2B. In one example embodiment, the actuation fibers 306 and 308 have angled gratings written into the core over actuation extent 352 and 358, which couple optical energy into the respective adjacent SMA 362 and 354 (such as SMA wires 124/146 of FIGS. 1C and 1D, or SMA cylinders 202/206 of FIGS. 2A and 2B), generating thermal excitation which provides the SMA actuator deflection as was previously described. Deflection sensor 360 and temperature sensor 358 may both be formed into a single fiber as shown, using Bragg gratings operative at unique wavelengths, which are coupled to sensing fiber 310. In one form of operation, excitation source 302 is periodically pulsed or operated continuously at a unique wavelength which does not interfere with temperature measurement using deflection sensor 360 and temperature sensor 358, both of which receive broadband optical energy from broadband source 304, which is coupled through circulator 308 to gratings 358 and 360, respectively. Reflected optical energy is coupled through circulator 308 to wavelength discriminator 306, which converts the wavelength shift to a needle shape such as by using a strain and temperature measurement from the Bragg grating sensors 358 and 360.

The preceding has been a description of the preferred embodiment of the invention. It will be appreciated that deviations and modifications can be made without departing from the scope of the invention, which is defined by appended claims.

We claim:

1. A biopsy needle comprising:
an outer sleeve cannula surrounding a removable steerable stylet;
said removable steerable stylet comprising an outer stylet part and an inner stylet part, said outer stylet part comprising a cylindrical shell having a central axis and a medial plane which lies on the central axis, said cylindrical shell also having an axial deflection extent formed by a plurality of slots formed into the cylindrical shell which are substantially perpendicular to the central axis and also substantially perpendicular to the medial plane, the slots having a circumferential extent which passes through said medial plane, said slots formed on both sides of the medial plane, the circumferential extent of the slots arranged to have a circumferential midpoint located on opposite sides of the medial plane, the slots thereby providing elastic bi-directional bending of the outer stylet part in a plane substantially perpendicular to the medial plane;

said outer stylet part having a shape memory alloy (SMA) which is attached to the cylindrical shell at opposite ends of the deflection extent;

said inner stylet part also having a shape sensing optical fiber comprising an optical fiber with a reflective end and a series of slits in cladding of the shape sensing optical fiber which are perpendicular to an axis of the shape sensing optical fiber, the inner stylet part being optically transparent for infrared optical energy;

whereby when the SMA is thermally activated from optical energy in an actuation optical fiber positioned a separation distance from the SMA and optically coupled to the SMA, the biopsy needle deflects in a direction which reduces a width of the slots on one side of the medial plane or on the opposite side of the medial plane;

the biopsy needle deflection causing a change in the transmissivity of the shape sensing optical fiber.

2. The biopsy needle of claim 1 where said SMA is a wire attached to an inner surface of the outer stylet part on opposite ends of the deflection extent, the SMA configured to receive the optical energy from the the actuation optical fiber of the inner stylet part and also configured to receive optical energy reflected from the inner surface of the outer stylet part, the actuation optical fiber coupling optical energy to the SMA to cause said thermal activation of the SMA.

3. The biopsy needle of claim 2 where said SMA is a cylindrical tube and said actuation optical fiber is located inside said cylindrical tube such that said SMA surrounds said actuation optical fiber, said actuation the optical fiber coupling optical energy to said SMA, which thermally activates and causes a deflection of the outer stylet part.

4. The biopsy needle of claim 2 where said inner stylet part or said outer stylet part has a reflective gold surface applied which reflects the optical energy inside said inner stylet part or said outer stylet part to said SMA.

5. The biopsy needle of claim 1 where said inner stylet part includes a temperature sensor and a deflection sensor, the actuation optical fiber coupling the optical energy to the SMA and actuating the SMA, the temperature sensor and deflection sensor each being a fiber Bragg grating (FBG) which reflects narrowband optical energy to indicate a temperature or a deflection.

6. The biopsy needle of claim 1 where said SMA is an alloy of nickel-titanium or an alloy of copper-aluminum-nickel formed into wire.

7. The biopsy needle of claim 1 where said actuation optical fiber is multi-mode fiber.

8. The biopsy needle of claim 1 where said actuation optical fiber has a side-polished region to remove cladding from said actuation optical fiber, thereby coupling the optical energy to said SMA.

9. The biopsy needle of claim 1 where said actuation optical fiber has a tilted fiber Bragg grating which directs the optical energy from said actuation optical fiber to said SMA.

10. The biopsy needle of claim 1 where said outer sleeve cannula has an asymmetric tip.

11. The biopsy needle of claim 1 where said inner stylet part is formed from polytetrafluoroethylene (PTFE).

12. The biopsy needle of claim 1 where said actuation optical fiber carries the infrared optical energy for activation of said SMA.

13. The biopsy needle of claim 1 where said deflection is estimated using the shape sensing optical fiber, the shape sensing optical fiber positioned in the inner stylet part, said shape sensing optical fiber having a sensing port on one end opposite the reflective end, the reflective end of the shape sensing optical fiber coated with sputtered gold, the shape sensing optical fiber positioned in the inner stylet part, said series of slits in the shape sensing optical fiber positioned within said deflection extent, whereby deflection of said biopsy needle is estimated by measuring the optical loss for optical energy inserted into said sensing port and reflected to said sensing port.

14. A biopsy needle comprising:

an outer cannula having a central axis, the outer cannula having, in sequence, an asymmetric tip, a deflection extent, and a base, the asymmetric tip having a beveled surface with respect to the central axis;

an outer stylet including a deflection extent comprising a plurality of slots formed above and below a medial plane which lies on said central axis, said outer stylet deflection extent including a plurality of shape memory alloy (SMA) wires directly attached to an inner surface of the outer stylet at opposite ends of the outer stylet deflection extent, the SMA wires changing dimension or shape in response to applied thermal energy, each SMA wire attached on opposite inner surfaces of the outer stylet on a respective side of said medial plane;

an inner stylet placed inside said outer stylet, the inner stylet having at least one actuation optical fiber positioned a separation distance from the plurality of SMAS, the at least one actuation optical fiber optically coupled to a respective said SMA wire of said outer stylet through the inner stylet, the inner stylet transparent for transmission of optical activation energy;

whereby optical energy coupled into one said actuation optical fiber is coupled to a respective said SMA, causing the SMA to change shape to provide a deflection of said asymmetric tip from said central axis.

15. A biopsy needle having an outer sleeve cannula enclosing an outer stylet and an optically transparent inner stylet;

the outer stylet attached to a base portion, the outer stylet having a plurality of slots which are perpendicular to an outer stylet central axis, the slots formed above and below a medial plane on said central axis, the slots arranged to have a circumferential midpoint located on opposite sides of the medial plane, the outer stylet further comprising:

a deflection extent and an asymmetric tip;

a Shaped Memory Alloy (SMA) wire placed on at least one side of the medial plane and directly attached to an inner surface of the outer stylet on opposite ends of said deflection extent;

the inner stylet comprising:

at least one actuation optical fiber coupling optical energy to the SMA wire through the optically transparent inner stylet, the actuation optical fiber placed adjacent to the SMA wire;

at least one optical fiber for measuring a temperature; and at least one deflection sensing optical fiber for measuring a deflection, the deflection sensing optical fiber comprising a reflective end and a series of slits in cladding of the deflection sensing optical fiber which are perpendicular to an axis of the deflection sensing optical fiber.

16. The biopsy needle of claim 15 where said SMA wire is formed from a nickel-titanium alloy or a copper-aluminum nickel alloy.

17. The biopsy needle of claim 15 where said actuation the optical fiber coupling optical energy to the SMA wire is a multi-mode optical fiber.

18. The biopsy needle of claim 15 where said actuation optical fiber is side polished on at least one surface to couple the optical energy from said actuation optical fiber to said SMA wire.

19. The biopsy needle of claim 15 where said actuation optical fiber coupling the optical energy to the SMA wire has a tilted fiber Bragg grating for coupling the optical energy from said actuation optical fiber to said SMA wire.

20. The biopsy needle of claim 15 where said SMA wire or said outer stylet is formed from a superelastic material.

* * * * *